(12) United States Patent
Holmberg et al.

(10) Patent No.: US 8,106,185 B2
(45) Date of Patent: Jan. 31, 2012

(54) MODIFIED HYDROXYPOLYMER CONJUGATES WITH KILLING EFFECT ON TUMOR CELLS

(75) Inventors: Anders Holmberg, Uppsala (SE); Lennart Meurling, Stockholm (SE)

(73) Assignee: Dextech Medical AB, Uppsala (SE)

( * ) Notice: Subject to any disclaimer, the term of this patent is extended or adjusted under 35 U.S.C. 154(b) by 336 days.

(21) Appl. No.: 12/043,503

(22) Filed: Mar. 6, 2008

(65) Prior Publication Data

US 2008/0221066 A1 Sep. 11, 2008

(30) Foreign Application Priority Data

Mar. 7, 2007 (FI) ...................................... 20075158

(51) Int. Cl.
C08B 37/02 (2006.01)
A61K 31/721 (2006.01)
A61P 35/04 (2006.01)

(52) U.S. Cl. ....................................................... 536/112

(58) Field of Classification Search ........................ None
See application file for complete search history.

(56) References Cited

U.S. PATENT DOCUMENTS

| | | | |
|---|---|---|---|
| 6,033,719 A | 3/2000 | Keogh | |
| 6,288,124 B1* | 9/2001 | Kaddurah-Daouk | 514/634 |
| 6,569,841 B1* | 5/2003 | Holmberg | 514/59 |
| 2001/0027237 A1 | 10/2001 | Mayes et al. | |
| 2002/0107363 A1 | 8/2002 | Fox et al. | |
| 2005/0090553 A1 | 4/2005 | Shapiro | |
| 2006/0002974 A1 | 1/2006 | Pacetti et al. | |

FOREIGN PATENT DOCUMENTS

| | | |
|---|---|---|
| CN | 14755210 A | 2/2004 |
| FR | 2309556 A1 | 11/1976 |
| WO | 9745401 A1 | 12/1997 |
| WO | 0021571 A1 | 4/2000 |
| WO | 0023023 A1 | 4/2000 |
| WO | 2006136450 A2 | 12/2006 |

OTHER PUBLICATIONS

Joseph Satriano, Annals New York Academy of Sciences "Agmatine: At the Crossoroads of the Arginine Pathways", vol. 1009, pp. 34-43 (2003).*
Michel Auguet et al., Jpn. J. Pharmacol. "Selective Inhibition of Inducible Nitric Oxide Synthase by Agmatine", vol. 69, pp. 285-287 (1995).*
Gerhard J. Molderings et al., Cancer "Intestinal Tumor and Agmatine (Decarboxylated Arginine)", vol. 101, issue 4, pp. 858-868 (Aug. 2004).*
Wang & al., Inhibitory effect of agmatine on proliferation of tumor cells by modulation of polyamine metabolism. Acta Pharmacologica Sinica, 2005; 26(5), 618-622.
Zenteno-Savin et al., Effects of arginine vasopressin in the heart are mediated by specific intravascular endothelial receptors, European Journal of Pharmacology, 410:15-23 (2000).
Sherwood et al., Enhanced plasma persistence of therapeutic enzymes by coupling to soluble dextran, Biochem. J., 164:461-464 (1977).
Meurling et al., Polymer-conjugated guanidine is a potentially useful anti-tumor agent, International journal of Oncology, 35:281-285 (2009).

* cited by examiner

*Primary Examiner* — Shaojia Anna Jiang
*Assistant Examiner* — Bahar Schmidtmann
(74) *Attorney, Agent, or Firm* — Browdy and Neimark, PLLC

(57) ABSTRACT

The present invention is related to a modified hydroxypolymer conjugates preferably a guanidine-dextran conjugate having a tumor cell killing activity. The modified hydroxypolymer conjugate is used as medicine, particularly for manufacturing a medicine or tumor killing composition for treating tumors. A method for producing said hydroxypolymer conjugate and a method for killing cancer cells and treating tumors is also disclosed. The invention is also related to a method for killing tumor cells and treating tumors by administering an effective amount of the modified hydroxypolymer conjugate.

18 Claims, 6 Drawing Sheets

MODIFIED HYDROXYPOLYMER CONJUGATES WITH KILLING EFFECT ON TUMOR CELLS

TECHNICAL FIELD OF INVENTION

The present invention is related to a modified hydroxypolymer conjugate, particularly a guanidine-dextran conjugate having a tumor killing effect, and a method for preparation of said conjugates as well as its use.

BACKGROUND OF INVENTION

Guanidine compounds have many interesting and important biomedical effects and consequently many uses. They are for example used as free radical scavengers, inhibitors of nitric oxide synthase (NOS) preventing nitric oxide formation. They are known to have certain anti-proliferative effects on cells. The guanidines are also used as "anti-aging" drugs, wherein the effect is achieved by protection from low density lipoprotein oxidation, by prevention of atherosclerotic lesions formation, by retarding the tissue damaging effects of diabetes, e.g. cardiovascular damage, through inhibition of the formation of advanced glycosylation end products (AGE's) as described in the following scientific publications (Yildiz et al. Br J Pharmacol, 1998 July; 124 (5): 905-910; Scaccini et al, J lipid Res, 1994, Vol 35, 1085-1092; Higashi et al, J Biochem, 2004, Vol 136, No 4, 533-539; Szende et al, Cancer Cell Int, 2001, 1:3; Sell et al, J Gerontol Soc Am, 2001, 56: B405-B411; Wang et al, World J Gastroenterol. 2005, Jul. 7:11, (25) 3830-3833; Zhang et al, World J Gastroenterol. 2001, Jun. 7, 3):331-334; J P Beissweniger, Dartmouth Med, http//dartmed.dartmouth.edu/summer00/html/bench_to_bedside.shtml. Aminoguanidine is currently supplied as a non-prescription drug in the United States and its role in the treatment of various diseases is investigated in clinical studies. The inhibitory effect of agmatine on proliferation of tumor cells by modulation of polyamine metabilism is described in Wang et al., Acata Pharmacologica Sinica 2005, May; 26(5): 616-622.

Since more than five decades dextran is an established pharmaceutical used for preventing hypovolemic chock, preventing embolism and improving microcirculation. Dextran and its non-toxic properties and high tolerability is very well documented (A S Segal, 1964 In: Modern medical monographs, ed. Wright, I S, Green & Stratton, NY, London, pp 5-17. Therefore, it is often used as an example of pharmaceutically applicable hydroxypolymers.

SUMMARY OF INVENTION

Guanidine compounds and dextrans have almost no toxic effect on tumor cells as shown in FIG. 1. However, it was surprisingly found that when the guanidine compounds were covalently conjugated to an activated hydroxypolymer, such as an activated dextran, the conjugates demonstrated a high antitumor efficacy, which was similar or at some dosages even higher than that of conventional antitumor drugs, like Adriamycin®.

Accordingly, the present invention is related to a modified hydroxypolymer conjugate having a tumor cell killing effect. The modified hydroxypolymer conjugate is a hydroxypolymer, such as a dextrin substituted with guanidine compounds, which have at least one free amino group and which are covalently coupled to activated hydroxyl groups of the hydroxypolymer moiety.

Preferred guanidine compounds in the present invention are agmatine or aminoguanidine and the hydroxypolymer moiety is a dextran, which has a molecular weight in the range $10^3$-$10^6$ Daltons and which is activated before being substituted with said guanidine compounds.

The modified hydroxypolymer conjugate may further comprise covalently coupled functional groups, including radio-nuclides, therapeutic compounds, anticancer drugs, targeting agents, etc.

The modified hydroxypolymer conjugate is preferably a guanidine-dextran conjugate having an average molecular weight of approximately 70 kD±25 kD, wherein 15-60%, preferably 20-50% of the glucose moieties of the dextran are substituted with guanidine compounds having at least one free amino side group, Said guanidine compounds, preferably agmatine or aminoguanidine are covalently coupled to activated hydroxyl groups of the said dextran. The hydroxypolymer conjugates may further comprise covalently coupled functional groups, including radio-nuclides, therapeutic compounds, anticancer drugs, targeting agents, etc. Useful targeting agents are for example biphosphonates, e.g. alendronate.

The present invention is also related to a method of killing tumor cells or treating tumors by using said hydroxypolymer conjugates as medicines, such as tumor killing compositions. The medicines are tumor killing compositions, which comprise the modified hydroxypolymer conjugate and at least pharmaceutically acceptable adjuvant. The medicines or tumor killing compositions are locally, intravesically, regiolocally, peritoneally, intratumorally, systemically or intravenously administrable. The medicines may further comprise covalently coupled functional groups, including radio-nuclides, therapeutic compounds, anticancer drugs, targeting agents, etc.

The present invention also provides a method for producing the modified hydroxypolymer conjugate. In the present method a guanidine compound having at least one free amino group is mixed with an eluent obtained when purifying an activated hydroxypolymer by gel filtration. The hydroxypolymer is activated by an oxidative reaction, wherein a periodate salt is added to an aqueous solution comprising said hydroxypolymer with subsequent addition of concentrated sulphuric acid and by ending the reaction by adding ethylene glycol. The hydroxypolymer, which has been activated as described above, is subsequently purified by gel filtration.

DETAILED DESCRIPTION OF INVENTION

Figure 1:
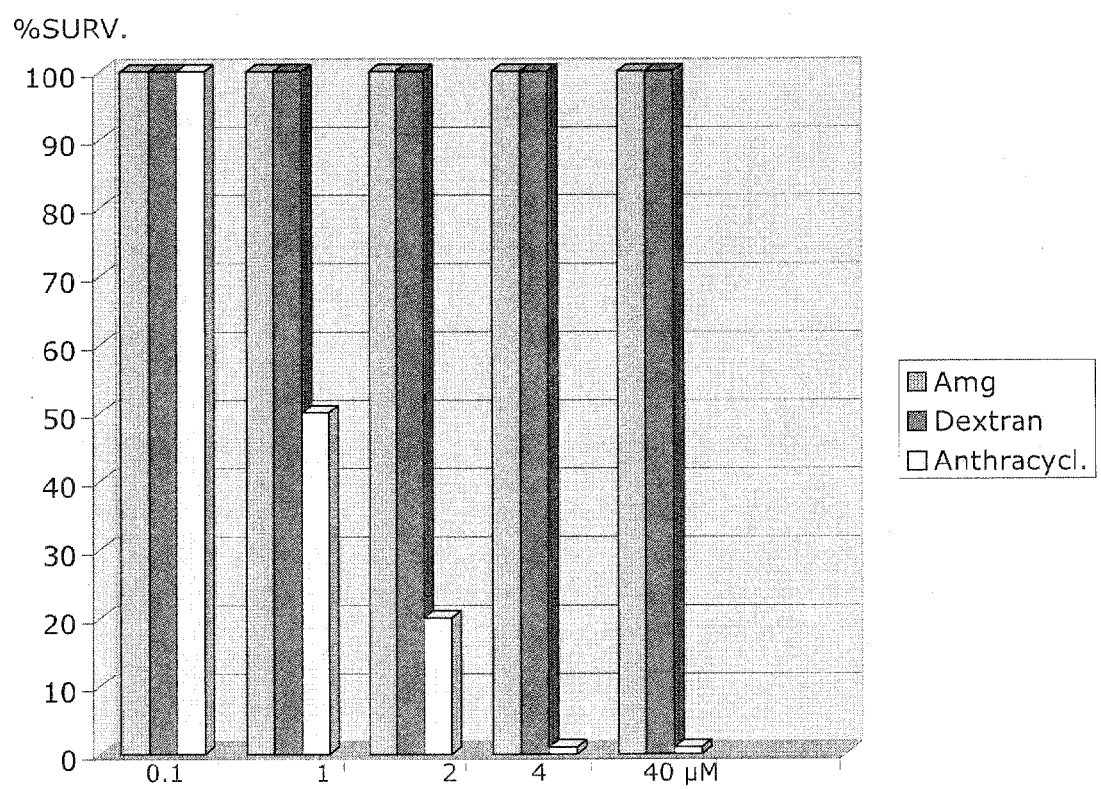
FIG. 1 demonstrates the toxic effect of dextran and aminoguanidine as compared to anthracycline=Adriamycin® using living urothelial cancer cells (RT4, ATCC, Manassas, USA). Percent survival is plotted on the y axes and incubation concentration is plotted on the x axes.

The inventors have discovered that certain guanidine compounds, having very low intrinsic toxicity, when covalently conjugated to a non-toxic hydroxyl polymer, such as dextran, have a high tumor cell killing efficacy. The tumor cell killing efficacy is equal to established anthracycline anticancer pharmaceuticals such as Farmorubicine® and Adriamvcine® or at some concentrations higher than established anticancer drugs. It appears probable that due to the harmless nature of the constituents of said polymer-guanidine conjugates, the handling of such conjugates i.e. for medical staff and the treatment connected side-effects for the patients can be expected to be favourable in comparison to conventional chemotherapeutic anti-cancer pharmaceuticals.

Targeting or tumor cell selectivity is believed to be achieved through the increased metabolic needs of the fast dividing tumor cells, which require amino-5-guanidinopentanoic acid and structurally related guanidine compounds and other constituents for polyamine formation (D Scott Lind, Am Soc Nutr Sci, 2004, J Nutr, 134:2837-2841; F Wayne, Turk J Med Sci, 2003, 33, 195-205). Cellular uptake of said guanidine compounds is mediated principally via the Na+-independent basic amino acid transport system y+ (Cendan et al, Ann Surg Oncol, 1995, 2:257-265).

The guanidine-polymer-conjugate of the present inventions is a compound, which as a backbone compound has a hydroxypolymer such as dextran. The molecular weight of hydroxylpolymer or dextran is between $10^3$-$10^6$ Daltons. Typically, the hydroxypolymer or dextran is substituted with between 15 to 60%, preferably between 20 to 50% guanidine side groups, i.e. 20-50% of the glucose moieties in the dextran backbone are substituted with guanidine groups.

In one analyzed batch, it was demonstrated that 100 mg aminoguanidine-dextran-conjugate, where the dextran polymer has a mean molecular weight of 70 kD, about 30 mg constitutes guanidine side groups. In other words, 273 μmol aminoguanidine is coupled to 1.4 μmol of dextran70, which means that about 50% of the glucose moieties are substituted with a guanidine group. In another batch, it was found that 100 mg aminoguanidine-dextran-conjugate, where the dextran polymer has a mean molecular weight of 70 kD, about 10 mg constitutes guanidine side groups. In other words, 90 μmol aminoguanidine is coupled to 1.3 μmol of dextran70, which means that about 18% of the glucose moieties are substituted with a guanidine group.

The medicine is preferably administered locally, e.g. by intra-vesical administration, regiolocally, e.g. by administration to the peritoneal cavity, intratumorally, i.e. by injection directly into a solid tumor, or systemically, i.e. by intravenous administration. All these routes of administration are possible and dependent on the specific therapeutic application.

The present invention is also related to a method for killing tumor cells, wherein an affective amount of the modified hydroxypolymer, preferably a dextran-guanidine conjugate is administered to a subject in need. Accordingly the invention is also related to a method for treating tumors, wherein an effective amount of the tumor cell killing composition comprising the modified hydroxypolymer, preferably a guandine-dextran conjugate is administered to a subject in need of tumor treatment.

The hydroxyl polymer or dextran polymer is substituted using side groups of guanidine. The guanidine groups are covalently coupled to said dextran polymer via free amino side groups of the guanidine compounds. The substitution is preceded by activating said dextran polymer through oxidation, which enables the reaction with said free amino side groups forming bonds of guanidine compounds with subsequent reduction obtain stable amine bonds (Matsunaga et al, Nucl Med Viol. 2005, 32, 279-285).

In the exemplified case, the aminoguanidine forms a hydrazone bond with the hydroxypolymer or dextran polymer. The hydrazone bond can be further reduced, yielding a guanidino hydrazine bond. Suitable guanidine compounds are agmatine and aminoguanidine.

Other functional groups may be coupled additionally to said guanidine hydroxypolymer conjugate. These functional groups include therapeutic drugs radionuclides, such as, Tc-99m, I-131, Y-90, Re-188, Sm-153, hormones, hormone antagonists, such as Tamoxifen, peptides, such as somatostatin, toxins, monoclonal antibodies or fragments thereof, free radical scavengers, such as amifostine or proteins and further targeting agents. Coupling of such functional groups is achieved directly or via bifunctional chelates that have been coupled to the hydroxypolymer prior to the inclusion of functional groups.

EXAMPLE I

Dextran Activation

Pharmaceutical grade dextran PM70 (150 mg) was dissolved in 6 ml of water. Sodium periodate 120 mg, was added, followed by 25 μl of concentrated sulphuric acid. The combined solution was stirred for 30 minutes. Ethylene glycol, 75 μl, was added in order to stop the oxidation and destroy excess periodate, by reacting for a further 15 minutes. The activated dextran was purified from low-molecular components by gel filtration in one ml portions on PD-10 columns with 0.1 M acetate, pH 6.5, as an eluent. In each separation, 2 ml of activated dextran solution was obtained.

Conjugation

The eluent, 1 ml, obtained by the procedure above, was mixed with

A) agmatine sulphate, 110 mg, and sodium cyanoborohydride, 5 mg,
B) aminoguanidine hydrochloride, 65 mg.

The solutions were stirred over night at room temperature and separated from low-molecular components on PD 10 columns with PBS as eluent. From each reaction, two ml of purified conjugate solution was obtained.

Figure 2:
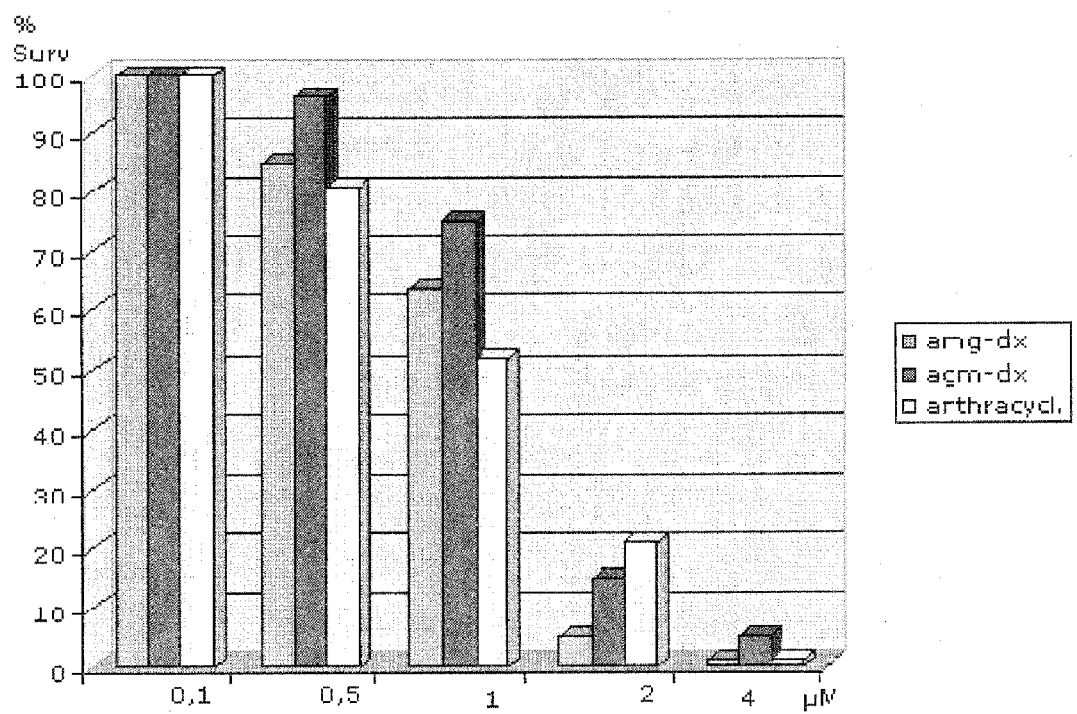
FIG. 2 shows the toxic effect of Guanidine-Dextran conjugates amgdx=aminoguanidine-dextran, agmdx=agmatine-dextran in comparison to anthracycline=Adriamncien® on urothelial cancer cells (RT4, ATCC, Manassas, USA). Percent survival is plotted on the y axes and incubation concentration is plotted on the x axes. The survival of urothelial cancer cells is $\leq 1=0$. The lower value means 100% cell death.
Figure 3:
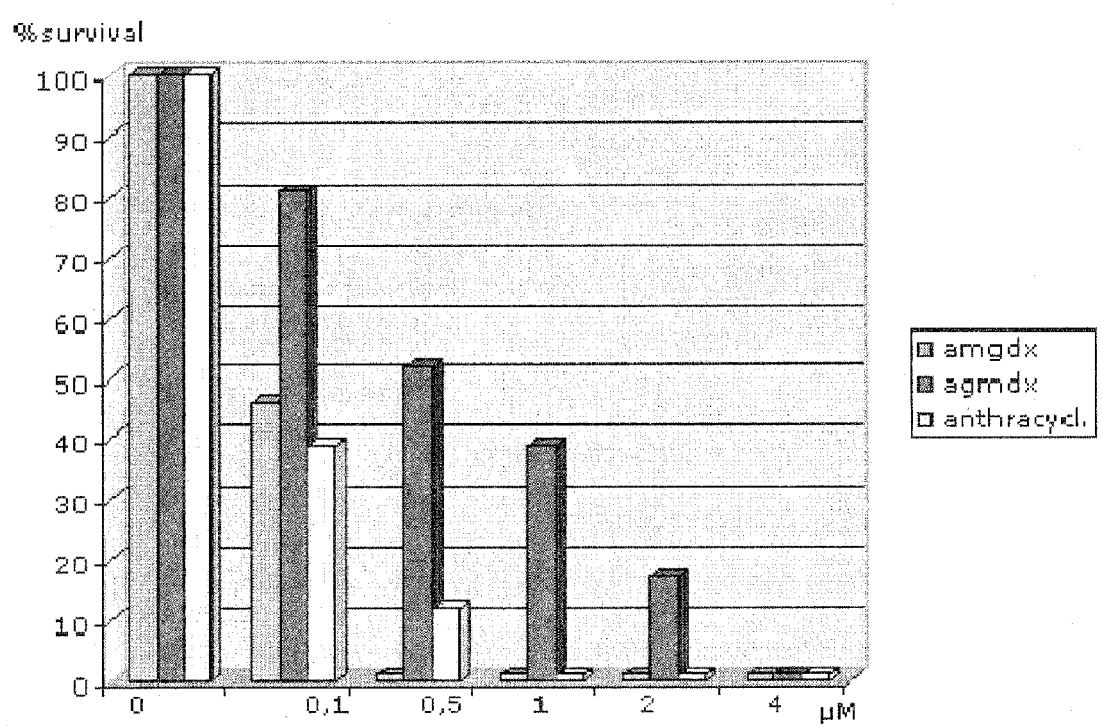
FIG. 3 shows the toxic effect of Guanidine-Dextran conjugates amgdx=aminoguanidine-dextran, agmdx=agmatine-dextran as compared to anthracycline.=Adriamycin® on urothelial cancer cells (5637, ATCC, Manassas, USA). Percent survival is plotted on the y axes and incubation concentration is plotted on the x axes. The survival of urothelial cancer cells is $\leq 1=0$.
Figure 4:
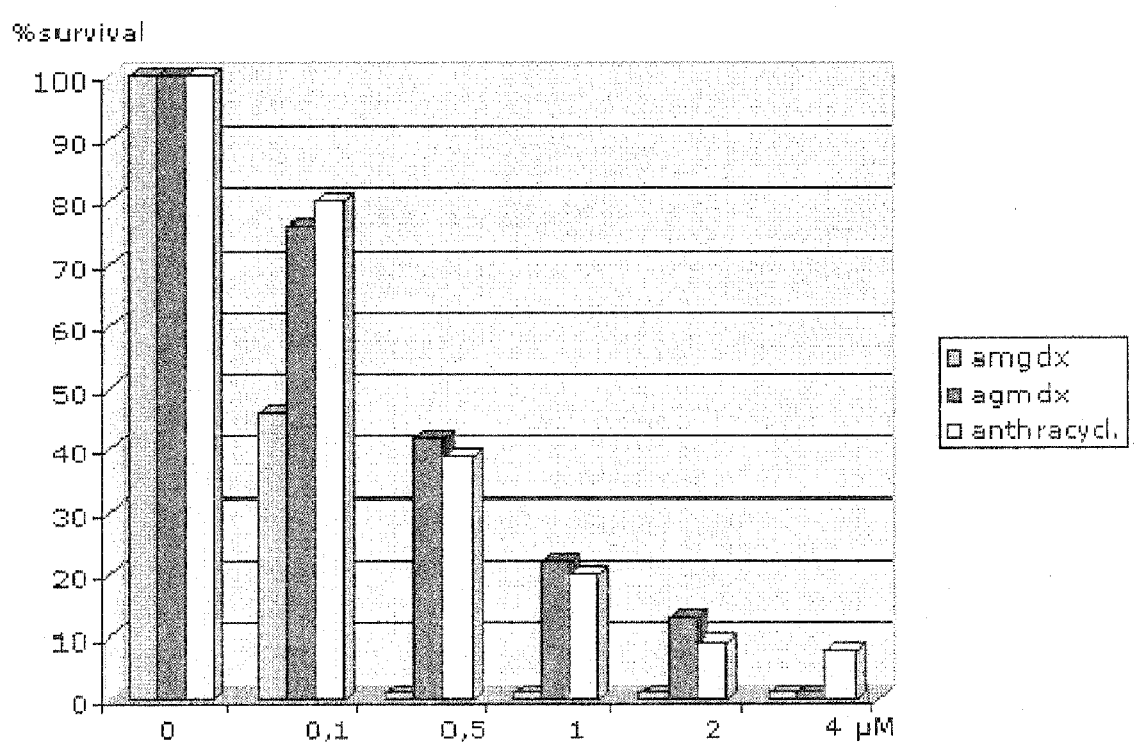
FIG. 4 shows the toxic effect of Guanidine-Dextran conjugates amgdx=aminoguanidine-dextran, agmdx=agmatine-dextran as compared to anthracycline.=Adriamycin® on prostate cancer cells (PC3, ATCC, Manassas, USA). The survival of prostate cancer cells is ≦1=0.
Figure 5:
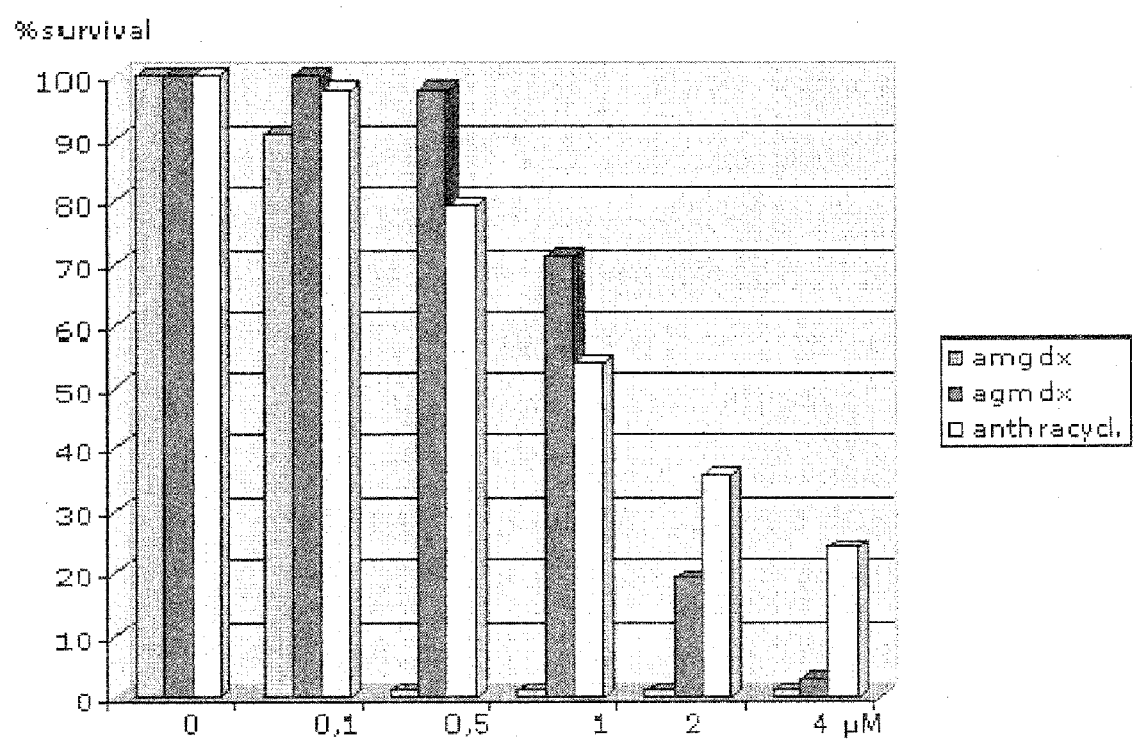
FIG. 5 shows the toxic effect of Guanidine-Dextran conjugates amgdx=aminoguanidine-dextran, agmdx=agmatine-dextran as compared to anthracycline.=Adriamycin®, on breast cancer cells (MDA231, ATCC, Manassas, USA). The survival of breast cancer cells is ≦1=0.
Figure 6:
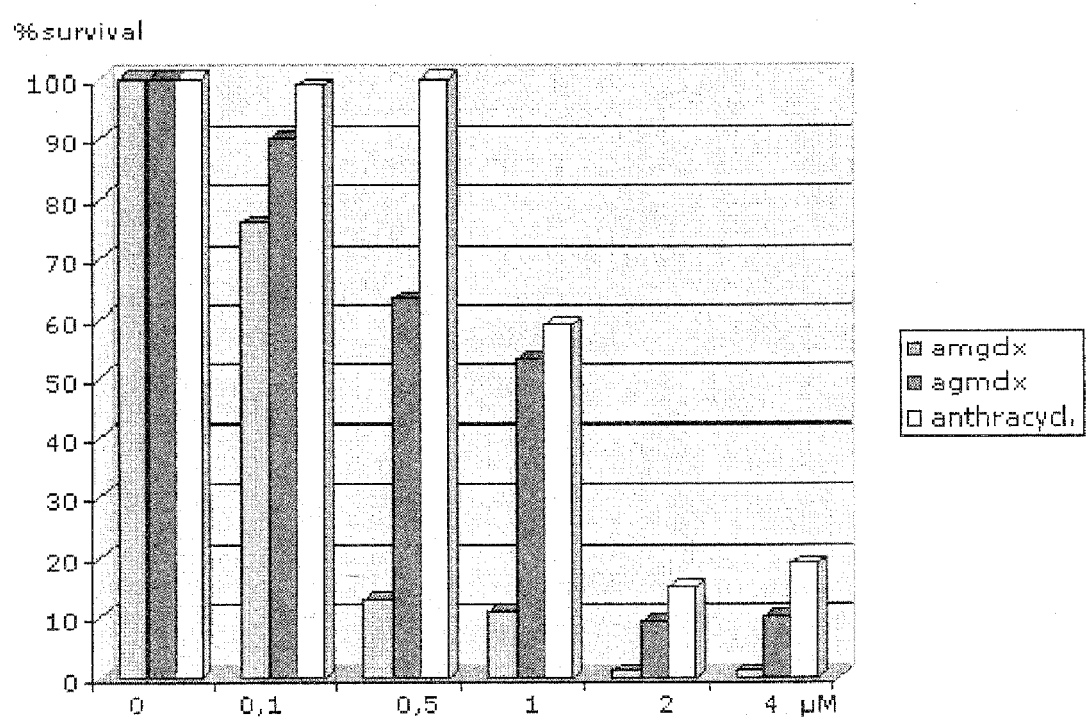
FIG. 6 shows the toxic effect of Guanidine-Dextran conjugates amgdx=aminoguanidine-dextran, agmdx=agmatine-dextran as compared to anthracycline.=Adriamycin® on renal cell cancer (A498, ATCC, Manassas, USA). The survival of renal cancer cells is ≦1=0 survival.

Fluorometric Cytotoxicity Assay (FIGS. 1-6)

The fluorometric cytotoxicity assay was performed as described by Larsson and Nygren (Larson et al, Anticancer Res, 1989, 9:1111-1119).

Briefly, approximately 10,000 cells/well were seeded (96-well microtiter plates, Falcon, Becton Dickinson, Meylan, France). Anthracycline and guanidine-dextran-conjugate with aminoguanidine or agmatine groups were added at equimolar concentrations (0.1, 0.5, 1, 2, and 4 µM). The control wells were given the same amount of PBS. After 72 h incubation the microtiter plates were centrifuged (200×g for 3 minutes) and the medium was removed by flicking the plates. The cells were washed in PBS. Fluorescein diacetate (FDA, Sigma, Stockholm, Sweden) was dissolved in DMSO and kept frozen at −20° C. as a stock solution (10 mg/ml). The FDA stock solution was diluted in PBS at a concentration of 10 µg/ml and 200 µl was added to each well. The plates were then incubated for 30 minutes at 37° C. A 96-well scanning fluorometer was used to count the emitted fluorescence from living cells. The data were transferred to a computer and the results were calculated. The results are shown in FIGS. 1-5, y axes showing % cell survival and x axes showing the molarity of the test substances.

The following tumor cell-lines were used (from ATCC, Manassas, US): RT4, 5637 (Urothelial cancer), MDA231 (Breast cancer), PC3 (Prostate cancer), A498 (Renal cell cancer).

The invention claimed is:

1. A modified hydroxypolymer conjugate having a tumor cell killing effect,
wherein the modified hydroxypolymer conjugate is a hydroxypolymer dextran in which 20-50% of the glucose moieties of dextran are substituted with guanidine compounds agmatine or aminoguanidine, which have at least one free amino group and which are covalently coupled to activated hydroxyl groups of said dextran moiety.

2. The modified hydroxypolymer conjugate according to claim 1, wherein said hydroxypolymer has a molecular weight of $10^3$-$10^6$ Daltons.

3. The modified hydroxypolymer conjugate according to claim 1,
wherein the modified hydroxypolymer conjugate is a guanidine-dextran conjugate having an average molecular weight of approximately 70 kD ±25 kD.

4. The modified hydroxypolymer conjugate according to claim 1, wherein the modified hydroxypolymer conjugate further comprises at least one covalently coupled functional group.

5. The modified hydroxypolymer according to claim 4, wherein said functional group is a radio-nuclide.

6. The modified hydroxypolymer according to claim 4, wherein said functional group is a therapeutic compound.

7. The modified hydroxypolymer according to claim 4, wherein said functional group is an anticancer drug.

8. The modified hydroxypolymer according to claim 4, wherein said functional group is a further targeting agent.

9. The modified hydroxypolymer conjugate according to claim 1, wherein said modified hydroxypolymer conjugate is locally, intravesically, regiolocally, peritoneally, intratumorally, systemically or intravenously administrable.

10. A composition having tumour cell killing effect, comprising the modified hydroxypolymer conjugate of claim 1 and at least one pharmaceutically acceptable adjuvant.

11. The modified hydroxypolymer conjugate according to claim 1, wherein said conjugate is produced by mixing a guanidine compound agmatine or aminoguanidine having at least one free amino group with an eluent comprising an activated dextran purified by gel filtration.

12. The modified hydroxypolymer conjugate according to claim 11, wherein the activated dextran is obtained by an oxidative reaction, wherein a periodate salt is added to an aqueous solution comprising dextran with subsequent addition of concentrated sulphuric acid and wherein the oxidative reaction is stopped by adding ethylene glycol, followed by purification with gel filtration.

13. The modified hydroxypolymer conjugate of claim 1, wherein the hydroxypolymer dextran is substituted with aminoguanidine.

14. The composition of claim 10, wherein the hydroxypolymer dextran is substituted with aminoguanidine.

15. A method for killing tumor cells, comprising administering an effective amount of the modified hydroxypolymer conjugate of claim 1 to a subject in need of tumor treatment, wherein the tumor cells are selected from the group consisting of urothelial tumor cells, breast tumor cells, prostate tumor cells and renal tumor cells.

16. A method for treating tumors, comprising administering an effective amount of the tumor cell killing composition of claim 10 to a subject in need of tumor treatment, wherein the tumors are selected from the group consisting of urothelial tumors, breast tumors, prostate tumors and renal tumors.

17. The method of claim 15, wherein the hydroxypolymer dextran is substituted with aminoguanidine.

18. The method of claim 16, wherein the hydroxypolymer dextran is substituted with aminoguanidine.

* * * * *